(12) United States Patent
Anderson et al.

(10) Patent No.: US 7,672,734 B2
(45) Date of Patent: Mar. 2, 2010

(54) NON-LINEAR ELECTRODE ARRAY

(75) Inventors: Meredith L. Anderson, Clifton Park, NY (US); Anne M. Pianca, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 369 days.

(21) Appl. No.: 11/396,309

(22) Filed: Mar. 31, 2006

(65) Prior Publication Data

US 2007/0150007 A1   Jun. 28, 2007

Related U.S. Application Data

(63) Continuation-in-part of application No. 11/319,291, filed on Dec. 27, 2005.

(51) Int. Cl.
*A61N 1/05* (2006.01)

(52) U.S. Cl. .................................................. 607/117
(58) Field of Classification Search ................. 607/116, 607/117
See application file for complete search history.

(56) References Cited

U.S. PATENT DOCUMENTS

| | | | |
|---|---|---|---|
| 3,718,142 A | 2/1973 | Mulier | |
| 3,724,467 A | 4/1973 | Avery et al. | |
| 4,286,249 A | 8/1981 | Lewis et al. | |
| 4,628,937 A * | 12/1986 | Hess et al. | 600/374 |
| 4,660,571 A * | 4/1987 | Hess et al. | 607/116 |
| 4,686,765 A | 8/1987 | Byers et al. | |
| 4,774,952 A * | 10/1988 | Smits | 607/2 |
| 4,907,601 A * | 3/1990 | Frick | 607/72 |
| 4,969,463 A * | 11/1990 | Dahl et al. | 607/5 |
| 5,193,539 A | 3/1993 | Schulman et al. | |
| 5,193,540 A | 3/1993 | Schulman et al. | |
| 5,312,439 A | 5/1994 | Loeb | |

(Continued)

FOREIGN PATENT DOCUMENTS

WO     WO 98/37926     9/1998

(Continued)

OTHER PUBLICATIONS

Deman, P. R. et al. "Design, Construction, and Mechanical Optimisation Process of Electrode with Radial Current Flow in the Scala Tympani." Journal of Neuroscience Methods. vol. 28, p. 143-150 (2003).

(Continued)

*Primary Examiner*—Kennedy J. Schaetzle
(74) *Attorney, Agent, or Firm*—Darby & Darby P.C.

(57) ABSTRACT

A system for stimulation includes an implantable pulse generator, a lead, and conductors. The lead includes an array body disposed at a distal end of the lead and electrodes concentrically arranged on the array body. A center electrode may also be disposed on the array body. The electrodes may be arranged in more than one concentric ring. A method of using an implantable stimulator includes implanting an implantable stimulator and providing an electrical signal to at least one electrode of the implantable stimulator to stimulate a tissue. The electrical signal may be provided between diametrically opposed electrodes or between electrodes that are not diametrically opposed. If the implantable stimulator has a center electrode, the electrical signal may be provided between the center electrode and at least one concentrically arranged electrode.

17 Claims, 5 Drawing Sheets

U.S. PATENT DOCUMENTS

| | | | | |
|---|---|---|---|---|
| 5,417,719 | A * | 5/1995 | Hull et al. | 607/46 |
| 5,817,030 | A * | 10/1998 | Tarjan et al. | 600/546 |
| 5,897,583 | A * | 4/1999 | Meyer et al. | 607/116 |
| 6,038,484 | A | 3/2000 | Kuzma | |
| 6,051,017 | A | 4/2000 | Loeb et al. | |
| 6,052,608 | A | 4/2000 | Young et al. | |
| 6,152,882 | A * | 11/2000 | Prutchi | 600/509 |
| 6,181,969 | B1 | 1/2001 | Gord | |
| 6,343,226 | B1 | 1/2002 | Sunde et al. | |
| 6,516,227 | B1 | 2/2003 | Meadows et al. | |
| 6,604,283 | B1 | 8/2003 | Kuzma | |
| 6,609,029 | B1 | 8/2003 | Mann et al. | |
| 6,609,032 | B1 | 8/2003 | Woods et al. | |
| 6,741,892 | B1 | 5/2004 | Meadows et al. | |
| 6,757,970 | B1 | 7/2004 | Kuzma et al. | |
| 6,961,622 | B2 | 11/2005 | Gilbert | |
| 7,006,859 | B1 * | 2/2006 | Osorio et al. | 600/378 |
| 7,010,356 | B2 * | 3/2006 | Jog et al. | 607/116 |
| 7,146,217 | B2 * | 12/2006 | Firlik et al. | 607/45 |
| 7,149,586 | B2 * | 12/2006 | Greenberg et al. | 607/116 |
| 7,221,981 | B2 * | 5/2007 | Gliner | 607/116 |
| 7,244,150 | B1 | 7/2007 | Brase et al. | |
| 7,305,268 | B2 * | 12/2007 | Gliner et al. | 607/45 |
| 2002/0128700 | A1 | 9/2002 | Cross | |
| 2003/0204228 | A1 | 10/2003 | Cross et al. | |
| 2004/0015221 | A1 | 1/2004 | Kuzma | |
| 2004/0043052 | A1 | 3/2004 | Hunter et al. | |
| 2004/0059392 | A1 | 3/2004 | Parramon et al. | |
| 2005/0004638 | A1 | 1/2005 | Cross | |

FOREIGN PATENT DOCUMENTS

| | | |
|---|---|---|
| WO | WO 98/43700 | 10/1998 |
| WO | WO 98/43701 | 10/1998 |
| WO | WO-0117315 | 3/2001 |

OTHER PUBLICATIONS

U.S. Appl. No. 11/238,240, filed Sep. 29, 2005.

U.S. Appl. No. 11/319,291, Official Communication mailed Dec. 24, 2008 (12 pages).

U.S. Appl. No. 11/319,291, Official Communication mailed Mar. 19, 2009 (11 pages).

* cited by examiner

NON-LINEAR ELECTRODE ARRAY

This application is a continuation-in-part of U.S. patent application Ser. No. 11/319,291, filed Dec. 27, 2005, incorporated herein by reference.

FIELD

The invention is directed to implantable stimulators. In addition, the invention is directed to implantable stimulators having electrodes arranged concentrically, and methods of using the devices.

BACKGROUND OF THE INVENTION

Stimulators have been developed to provide therapy for a variety of disorders, as well as other treatments. For example, stimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Stimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. Other stimulators, such as the Precision® rechargeable stimulator, in combination with linear/percutaneous leads or paddle type leads are used to stimulate the spinal cord for treating intractable chronic pain. It is preferable that the electronic circuitry and power source be held within the housing in a hermetically-sealed environment for the protection of the user and the protection of the circuitry and power source. Once implanted, it is often preferable that the stimulator can be controlled and/or that the electrical source can be charged without removing the stimulator from the implanted environment.

BRIEF SUMMARY OF THE INVENTION

In one embodiment, a lead includes an array body disposed at a distal end of the lead and electrodes concentrically arranged on the array body. The concentrically arranged electrodes may also be arranged symmetrically with respect to one or more central axes, arranged such that at least two electrodes are diametrically opposed, or arranged such that no two electrodes are diametrically opposed. A center electrode may also be disposed on the array body. The electrodes may be arranged in more than one concentric ring.

In another embodiment, a system for stimulation includes an implantable pulse generator, a lead, and conductors. The lead of the system for stimulation includes an array body disposed at a distal end of the lead and electrodes concentrically arranged on the array body. At least one of the conductors is attached to each electrode, and the conductors are configured and arranged to couple the electrodes to the implantable pulse generator.

In yet another embodiment, a method of using an implantable stimulator includes implanting an implantable stimulator and providing an electrical signal to at least one electrode of the implantable stimulator to stimulate a tissue. The implantable stimulator includes a lead. The lead includes an array body disposed at a distal end of the lead and electrodes concentrically arranged on the array body. The electrical signal may be provided such that the tissue is bilaterally stimulated. The electrical signal may also be provided between diametrically opposed electrodes or between electrodes that are not diametrically opposed. If the implantable stimulator has a center electrode, the electrical signal may be provided between the center electrode and at least one concentrically arranged electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

The invention is directed to implantable stimulators. In addition, the invention is directed to implantable stimulators having electrodes arranged concentrically, and methods of using the devices.

Examples of stimulators and stimulator systems are found in U.S. Pat. Nos. 6,609,032; 6,181,969; 6,516,227; 6,609,029; and 6,741,892; and U.S. patent application Ser. Nos. 11/238,240; 11/319,291; and 11/327,880, all of which are incorporated herein by reference.

In at least some applications, it is desirable that the electrodes of an implantable stimulator be arranged in a non-linear arrangement. For example, a non-linear arrangement of electrodes may be desirable when the tissue to be stimulated is not oriented in a straight line. A non-linear arrangement of electrodes may also facilitate effective positioning of an implantable stimulator relative to the tissue to be stimulated. For example, a non-linear electrode array that is circular may provide similar stimulation when positioned anywhere from 0 to 360 degrees. This may facilitate faster implantation by allowing greater latitude in placement of the lead and the electrodes.

Alternatively, or additionally, an implantable stimulator with a non-linear arrangement of electrodes may be desirable when it is advantageous to alter the electrode coverage area. For example, the electrode coverage area of concentrically arranged electrodes may provide a different electrode coverage area than a linear arrangement of the same electrodes, which may be desirable depending, for example, on the tissue to be stimulated. Non-linear electrode arrangements may also be particularly suited for stimulating certain tissues, such as when bilateral stimulation is desirable.

In at least some embodiments, a lead includes an array body disposed at a distal end of the lead and electrodes concentrically arranged on the array body. In some embodiments, the electrodes are arranged in more than one concentric ring. The array body may optionally include a centrally located electrode.

Figure 1:
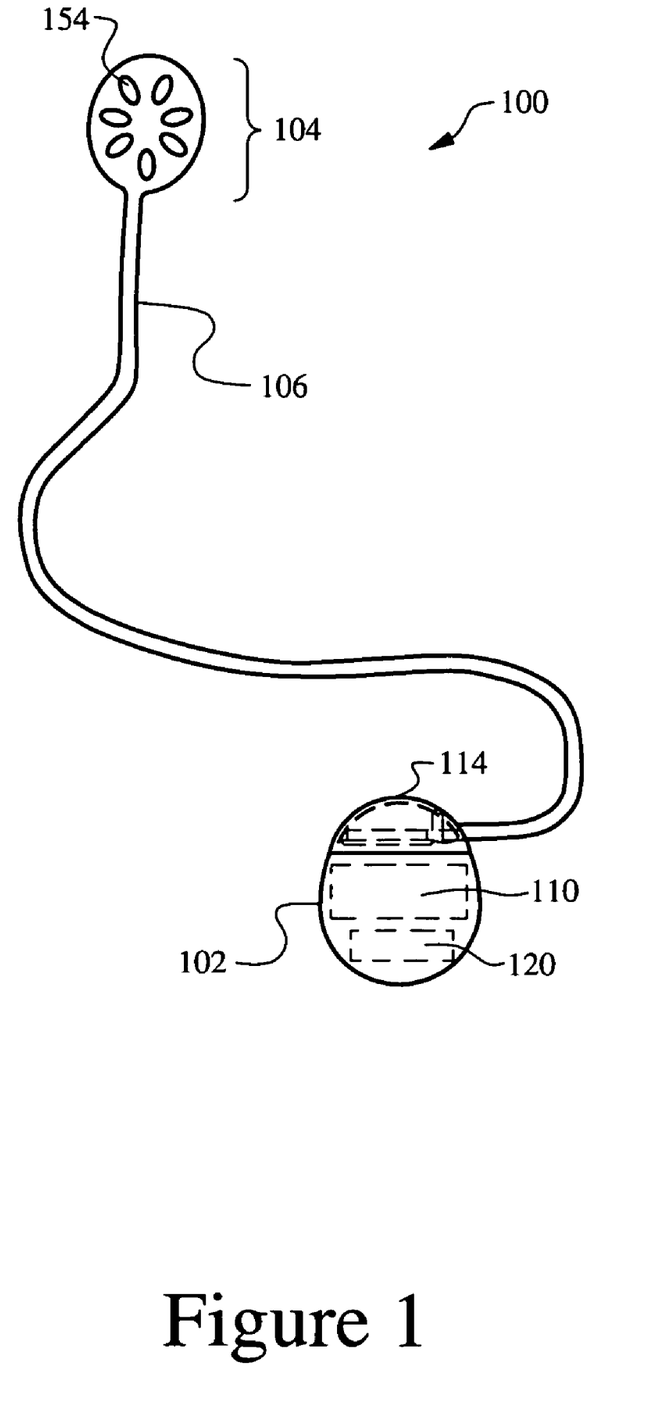
FIG. 1 is a schematic exterior perspective view of one embodiment of a system for stimulation, according to the invention.

FIG. 1 illustrates schematically one embodiment of a stimulation system 100. The stimulation system includes an implantable pulse generator 102, an array body 104, and at least one lead body 106 coupling the implantable pulse generator 102 to the array body 104. The array body 104 and the lead body 106 form a lead. It will be understood that the system for stimulation can include more, fewer, or different components and can have a variety of different configurations including those configurations disclosed in the stimulator references cited herein. The stimulation system or components of the stimulation system, including one or more of the lead body 106, the array body 104 and the implantable pulse generator 102, are implanted into the body.

The implantable pulse generator 102 typically includes a housing 114 with an electronic subassembly 110 and, in at least some embodiments, a power source 120 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive.

The housing 114 may be made of any biocompatible material including, for example, glass, ceramics, metals, and polymers. In one embodiment, the housing 114 is made from implantable grade titanium. In another embodiment, the housing 114 of the implantable pulse generator is formed of a plastic material that resists the transport of moisture into the interior of the housing and is sufficiently sturdy to protect the components on the interior of the housing from damage under expected usage conditions. Preferably, the material of the plastic housing is a hydrophobic polymer material. The housing 114 may include additives such as, for example, fillers, plasticizers, antioxidants, colorants, and the like. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the stimulator is implanted. (In another embodiment, the housing itself may include such a compound to be released over time after implantation.)

In one embodiment, a conductor or conductors (not shown) couple the electrode(s) 154 to the implantable pulse generator 102. The conductors can be formed using any conductive material. Examples of suitable materials include, for example, metals, alloys, conductive polymers, and conductive carbon. In one embodiment, the conductors are insulated by an insulating material, except for the portion of the conductor attached to the electrode 154, implantable pulse generator 102, or other components of the electronic circuitry. The insulating material may be any material that is a poor conductor of an electrical signal, including, for example, Teflon™, non-conductive polymers, or metal oxidation that is poor in electrical conductivity.

Figure 11:
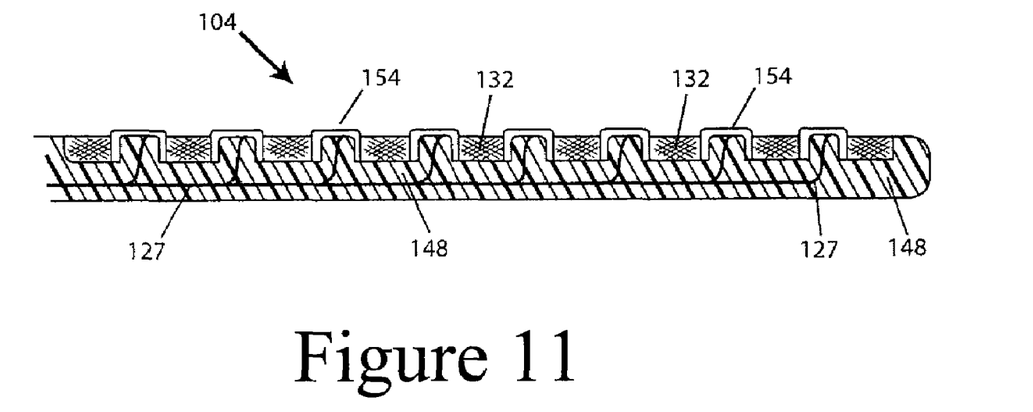
FIG. 11 is a schematic cross-sectional view of an exemplary array body.

The array body 104 may be made of any biocompatible material including, for example, silicone, polyurethane, polyetheretherketone (PEEK), epoxy, and the like. The array body 104 may be formed by any process including, for example, molding (including injection molding), casting and the like. In one embodiment, a method of making an array body is disclosed in U.S. patent application Ser. No. 11/319,291, which is incorporated herein by reference. Referring to FIG. 11, one example of a method of making a lead for a stimulation device includes forming an array of electrodes 154 in a pre-determined arrangement, forming a carrier 132 around the array, and placing a biocompatible material 148 over at least a portion of the carrier 132. In this method, an array of electrodes 154 is formed in a pre-determined arrangement in an array body 104. The carrier can be made of any biocompatible material including, for example, silicone, polyurethane, polyetheretherketone (PEEK), epoxy, and the like.

Preferably, conductors 127 are attached to the back side of the electrodes 154, which is the side of the electrode 154 opposite the side that will be exposed to the body tissue.

In one embodiment, the material used to form the carrier 132 and the biocompatible material 148 are the same material. For example, both the carrier 132 and the biocompatible material 148 could be silicone rubber. Alternatively, the material used to form the carrier 132 and the biocompatible material 148 may be different. Preferably, the biocompatible material 148 is capable of attaching to the carrier material without an additional adhesive. However, in some instances the carrier 132 material may be covered by an adhesive prior to adding the biocompatible material 148.

In at least some embodiments, the materials used to form the carrier 132 and the biocompatible material 148 have different properties. For example, the carrier 132 material and the biocompatible material 148 may have a different durometer, hardness, flexibility, rigidity, density, elasticity, etc. In one embodiment, the carrier 132 material and the biocompatible material 148 are the same material, but have different properties. For example, both the carrier 132 material and the biocompatible material 148 can be made of silicone rubber, but the silicone rubber used to form the carrier 132 material has a different durometer (e.g., a higher durometer) from the silicone rubber that is the biocompatible material 148.

Returning to FIG. 1, the array body 104 can have any shape including, for example, a circular, elliptical, square or rectangular shape. Preferably the array body is solid.

Electrodes 154 are disposed on the array body. The electrodes 154 can be made using any conductive material. Examples of suitable materials include, for example, metals, alloys, conductive polymers, and conductive carbon. The number of electrodes 154 disposed on the array body 104 may vary, depending on the application for which the electrodes 154 will be used (e.g., brain stimulation, neural stimulation, spinal cord stimulation, etc.). For example, there can be two, three, four, five, six, seven, eight, nine, ten, eleven, twelve, thirteen, fourteen, fifteen, sixteen, or more electrodes 154. As will be recognized, other numbers of electrodes 154 may also be used.

Figure 2:
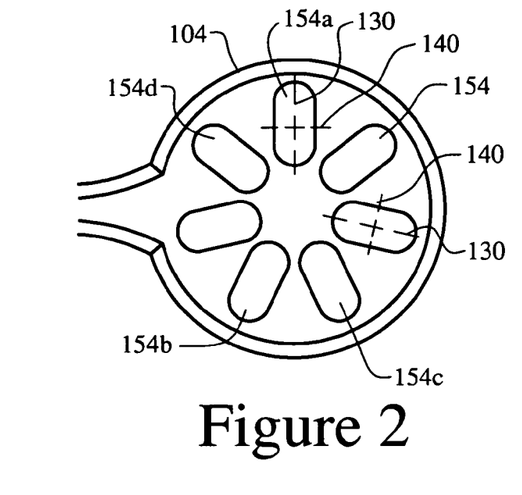
FIG. 2 is a schematic perspective view of one embodiment of an array body, according to the invention.

The electrodes 154 may have any shape including for example, a circular, elliptical, square, or rectangular shape. Circular electrodes 154 have a constant radius. In some embodiments, the electrodes 154 are non-circular. Non-circular electrodes often have a width that is not equal to the length of the electrode 154. In some embodiments, non-circular electrodes have a major axis 130 that bisects the larger dimension of the electrode and a minor axis 140 that bisects the smaller dimension of the electrode. The major axis 130 and the minor axis 140 of one example of a non-circular electrode are illustrated schematically in FIG. 2. As will be recognized, other non-circular electrodes are also possible. Alternatively, the electrodes 154 may be designed to have a shape that allows the electrode arrangement to follow the external boundary of the array body 104.

The electrodes 154 are arranged concentrically on the array body 104. The arrangement of the electrode(s) 154 on the array body 104 may vary. Electrodes 154 arranged concentrically on an array body 104 are arranged around a common center and can form circles or ellipses. In some embodiments, electrodes 154 arranged concentrically on an array body 104 are illustrated schematically in, for example, FIGS. 2, 3, 4, 5, 6, 7, 8, and 9. As will be recognized, other concentric arrangements of electrodes 154 are also possible.

Figure 3:
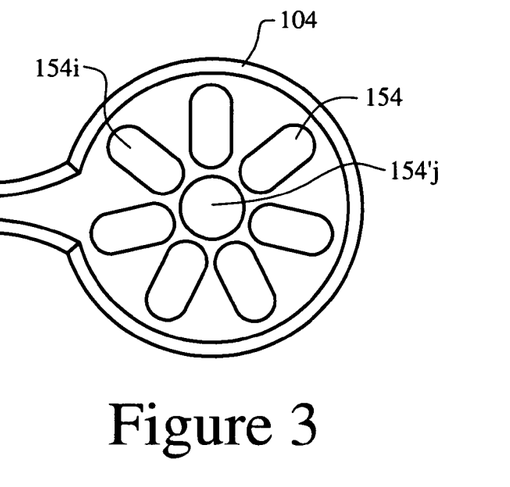
FIG. 3 is a schematic perspective view of a second embodiment of an array body, according to the invention.
Figure 5:
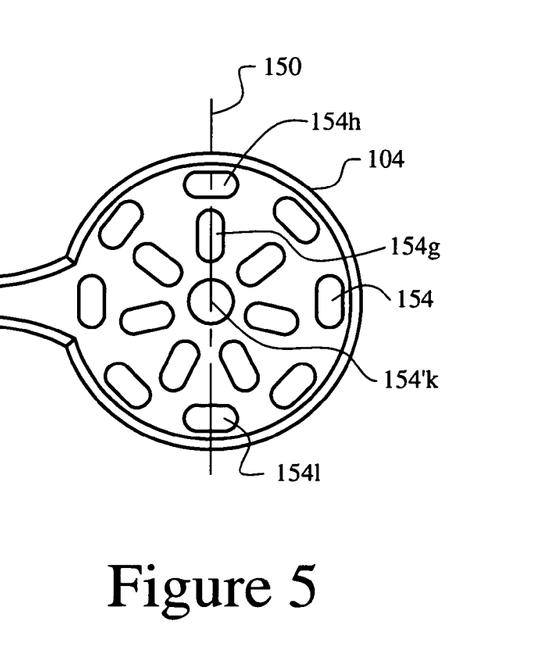
FIG. 5 is a schematic perspective view of a fourth embodiment of an array body, according to the invention.
Figure 9:
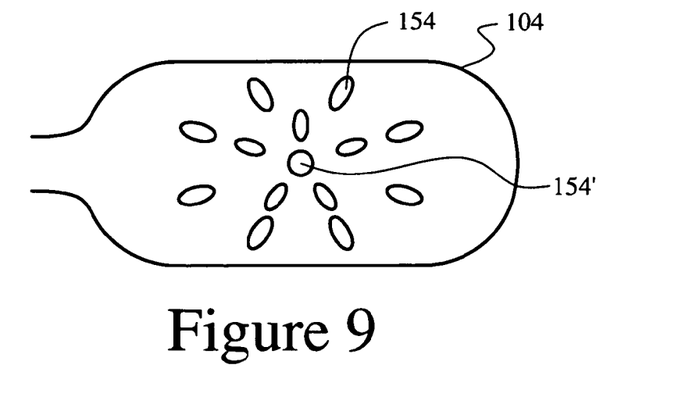
FIG. 9 is a schematic perspective view of an eighth embodiment of an array body, according to the invention.

Electrodes 154 may also be arranged on the array body 104 such that there is a centrally located electrode 154' as illustrated in FIGS. 3, 5 and 9. A centrally located electrode 154' is located at the common center of the concentrically arranged electrodes 154. For example, centrally located electrodes 154'j and 154'k are illustrated schematically in FIGS. 3 and 5, respectively.

Figure 4:
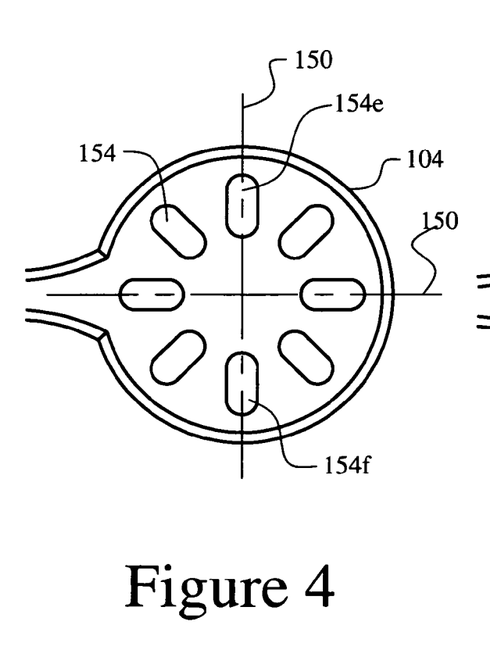
FIG. 4 is a schematic perspective view of a third embodiment of an array body, according to the invention.
Figure 6:
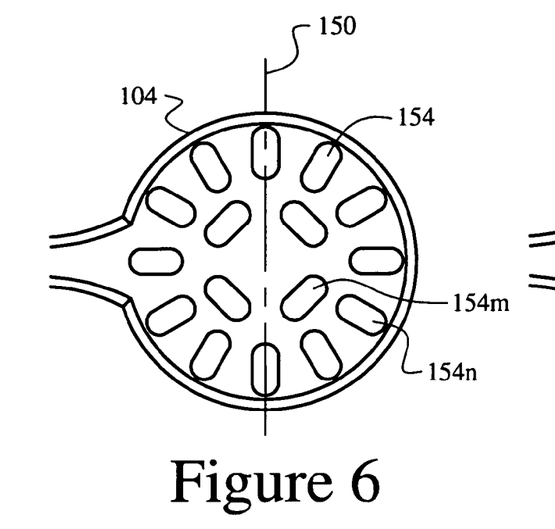
FIG. 6 is a schematic perspective view of a fifth embodiment of an array body, according to the invention.

Electrodes 154 may be arranged on the array body 104 symmetrically with respect to one or more central axes 150 as illustrated, for example, in FIGS. 4, 5 and 6. A central axis 150 bisects the arrangement of electrodes 154. When electrodes 154 are arranged on the array body 104 symmetrically with respect to a central axis 150, the electrodes 154 on one side of the central axis 150 are arranged in a mirror image of the electrodes 154 arranged on the opposite side of the central axis 150. As will be recognized, other symmetrical arrangements of electrodes 154 are also possible. An array body 104 with electrodes 154 arranged symmetrically with respect to one or more central axes 150 can have any shape.

Electrodes 154 may be arranged on the array body 104 such that at least two electrodes 154 are diametrically opposed. For example, electrode 154e and electrode 154f illustrated schematically in FIG. 4 are diametrically opposed. As will be recognized, other arrangements of electrodes 154 on an array body 104 in which at least two electrodes 154 are diametrically opposed are also possible. In other embodiments, no two electrodes 154 are diametrically opposed.

As will be recognized, electrodes 154 arranged with at least two electrodes 154 diametrically opposed may also be concentrically arranged. Electrodes 154 arranged with at least two electrodes 154 diametrically opposed may also be arranged symmetrically with respect to one or more central axes 150 as illustrated, for example, in FIG. 4. Likewise, electrodes 154 can be arranged symmetrically with respect to one or more central axes 150 such that no two electrodes 154 are diametrically opposed such as in FIGS. 2 and 3. An array body 104 with at least two electrodes 154 diametrically opposed or with no two electrodes 154 diametrically opposed can have any shape including, for example, a circular shape or an elliptical shape.

Figure 7:
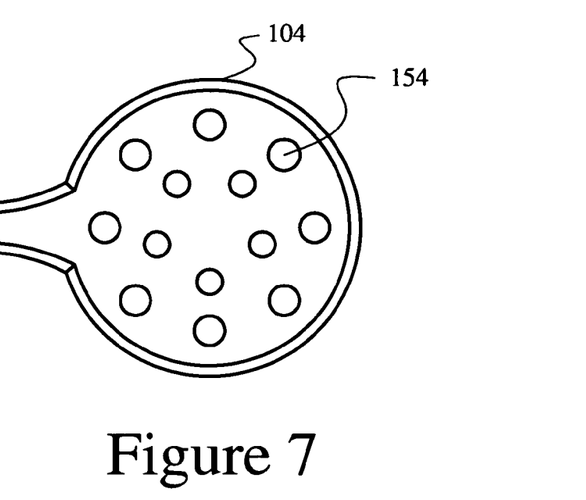
FIG. 7 is a schematic perspective view of a sixth embodiment of an array body, according to the invention.
Figure 8:
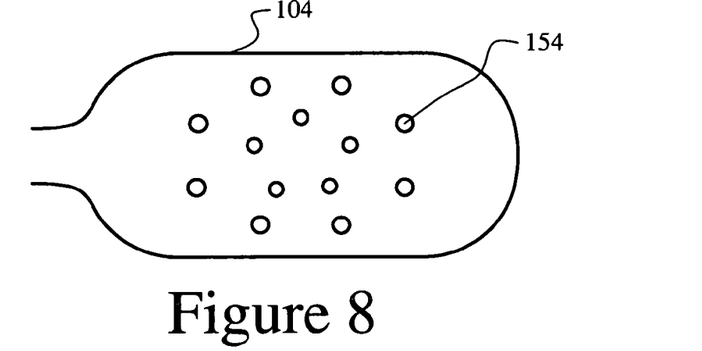
FIG. 8 is a schematic perspective view of a seventh embodiment of an array body, according to the invention.

Electrodes 154 may be concentrically arranged on the array body 104 in more than one concentric ring as illustrated, for example, in FIGS. 5-9. The concentric rings have a common center and each concentric ring may be in the shape of a circle or an ellipse. For example, electrodes 154 may be arranged concentrically in two or more circles that share a common center but have different radii, as illustrated in FIGS. 5, 6, and 7. Alternatively, electrodes 154 may be arranged concentrically in two or more ellipses as illustrated in FIGS. 8 and 9. In some embodiments, electrodes 154 may be concentrically arranged in more than one concentric ring, where the concentric rings have different shapes. For example, electrodes 154 may be arranged concentrically in an ellipse and a circle that share a common center.

An array body 104 may include electrodes 154 concentrically arranged on the array body 104 in more than one concentric ring in addition to having a centrally located electrode 154', electrodes 154 arranged symmetrically with respect to one or more central axes, and/or diametrically opposed electrodes 154.

Electrodes 154 may be non-circular electrodes. Non-circular electrodes are illustrated, for example, in FIGS. 2, 3, 4, 5, 6, and 9. For example, electrodes 154a, 154b, and 154c in FIG. 2, and electrode 154f in FIG. 4 are electrodes 154 that are non-circular. In some embodiments, non-circular electrodes have a minor axis 140 and a major axis 130. Non-circular electrodes may be arranged concentrically in more than one concentric ring as illustrated, for example, in FIGS. 5 and 6.

In some embodiments, the major axis 130 of at least one non-circular electrode in a first concentric ring is arranged radially and the major axis 130 of at least one non-circular electrode in a second concentric ring is arranged tangentially. For example, FIG. 5 illustrates a non-circular electrode 154g in a first concentric ring with its major axis 130 (see e.g. FIG. 2) arranged radially and a non-circular electrode 154h in a second concentric ring with its major axis 130 arranged tangentially.

Alternatively, the major axis 130 of at least one non-circular electrode in a first concentric ring may be arranged tangentially and the major axis 130 of at least one non-circular electrode in a second concentric ring may be arranged radially. For example, in FIG. 6, the major axis 130 of a non-circular electrode 154m in a first concentric ring is arranged tangentially and the major axis 130 of a non-circular electrode 154n in a second concentric ring is arranged radially. Non-circular electrodes can also be arranged in any configuration between tangential and radial orientations.

As will be recognized, an array body 104 may contain non-circular electrodes having a minor axis 140 and a major axis 130 in addition to having concentrically arranged electrodes 154, a centrally located electrode 154', electrodes 154 arranged symmetrically with respect to one or more central axes 150, electrodes 154 arranged in more than one concentric ring, and/or diametrically opposed electrodes 154. Likewise, an array body 104 with non-circular electrodes arranged concentrically in more than one concentric ring in which the major axis 130 of a non-circular electrode is arranged radially in a first concentric ring and a major axis 130 of another non-circular electrode in a second concentric ring is arranged tangentially may also have a centrally located electrode 154', electrodes 154 arranged symmetrically with respect to one or more central axes 150, and/or diametrically opposed electrodes 154. An array body having at least one non-circular electrode arranged radially and at least one non-circular electrode arranged tangentially can have any shape.

In some embodiments, at least one electrode 154 in a first concentric ring is aligned coaxially with at least one electrode 154 in a second concentric ring as illustrated, for example, in FIGS. 5 and 6. For example, in FIG. 5, electrode 154g in a first concentric ring is aligned coaxially with electrode 154h in a second concentric ring. In FIG. 5, electrode 154g in a first concentric ring is also aligned coaxially with electrode 154l in a second concentric ring. As will be recognized, other arrangements of electrodes in which an electrode in a first concentric ring is aligned coaxially with an electrode in a second concentric ring are possible. In other embodiments, no electrode in a concentric ring is aligned coaxially with an electrode in an adjacent concentric ring.

An array body 104 having concentrically arranged electrodes 154 with at least one electrode 154 in a first concentric ring aligned coaxially with at least one electrode in a second concentric ring may also have diametrically opposed electrodes 154, electrodes 154 arranged symmetrically with respect to one or more central axes 150, and/or a centrally located electrode 154'. An array body 104 having at least one electrode 154 in a first concentric ring aligned coaxially with at least one electrode in a second concentric ring may have any shape.

Figure 10:
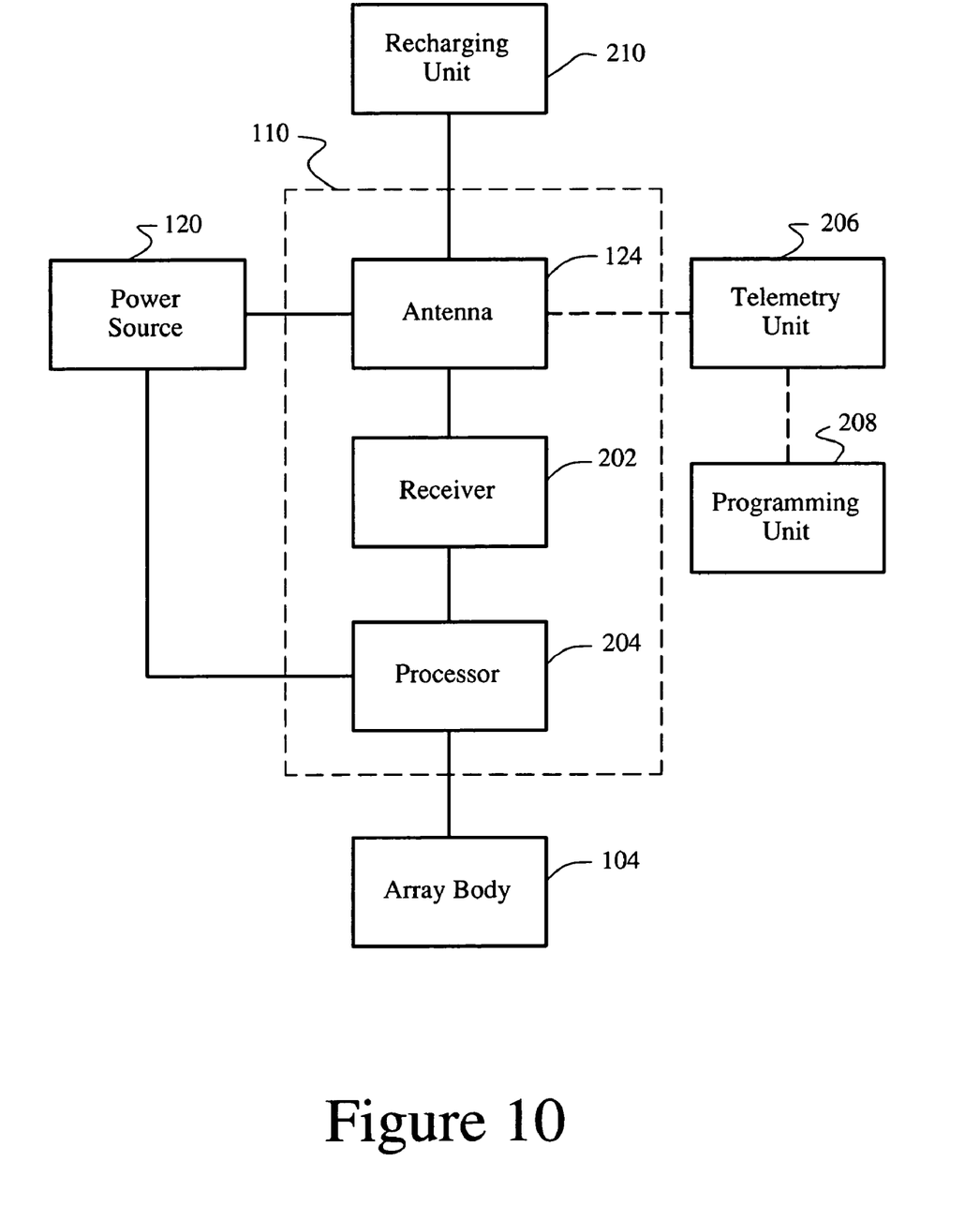
FIG. 10 is a schematic overview of components of a system for stimulation, according to an embodiment of the invention.

FIG. 10 is a schematic overview of one embodiment of components of a system for stimulation, including an electronic subassembly 110 (which may or may not include the power source 120), according to the invention. It will be understood that the system for stimulation and the electronic subassembly 110 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 120 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the stimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 10) external to the user.

In one embodiment, electrical current is emitted by the electrodes 154 to stimulate motor nerve fibers, muscle fibers, or other body tissues near the stimulator. The electronic subassembly 110 provides the electronics used to operate the stimulator and generate the electrical pulses at the electrodes 154 to produce stimulation of the body tissues. FIG. 10 illustrates one embodiment of components of the electronic subassembly and associated units.

In the illustrated embodiment, a processor 204 is generally included in the electronic subassembly 110 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 110 does not include an antenna 124 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

Any method of manufacture of the components of the system for stimulation can be used. For example, the power source and antenna can be manufactured as described in U.S. Patent Application Publication No. 2004/0059392. These components can then be placed inside the housing (or, alternatively, the housing can be formed, e.g., molded, around the components).

A stimulator can be implanted into a patient and electrical signals can be provided to the conductive electrode(s) 154 to stimulate a tissue. In one embodiment, a method of using an implantable stimulator includes implanting an implantable stimulator comprising a lead. The lead comprises an array body 104 disposed at a distal end of the lead. Electrodes 154 are concentrically arranged on the array body 104. An electrical signal is provided to at least one electrode 154 arranged on the array body 104 to stimulate a tissue.

An implantable stimulator can be implanted into the body tissue using a variety of methods including surgical methods. In some embodiments, the stimulator can be implanted using a hypodermic needle or other insertion cannula. Examples of insertion techniques can be found in U.S. Pat. No. 6,051,017.

An electrical signal may be provided to the electrodes 154 of an implantable stimulator having electrodes 154 concentrically arranged on an array body 104 such that a tissue is bilaterally stimulated. In other embodiments, two leads having array bodies 104 with concentrically arranged electrodes 154 may be used to bilaterally stimulate a tissue.

The stimulator electrodes 154 may be selectively stimulated. Electrical signals may be provided to the electrodes 154 of the stimulator simultaneously. Alternatively, electrical signals can be provided to the electrodes 154 of the stimulator independently of one another. Coordination of the electrical signals provided to the electrode(s) 154 is often facilitated by a processor 204.

An electrical signal may be provided to the electrodes 154 of an implantable stimulator such that the electrical signal is provided between electrodes 154 that are diametrically opposed. For example, an electrical signal can be provided between diametrically opposed electrodes 154e and 154f in FIG. 4. As will be recognized, an electrical signal could be provided to electrodes 154 in other arrangements in which at least two electrodes 154 are diametrically opposed.

An electrical signal may also be provided to the electrodes 154 of an implantable stimulator such that the electrical signal is provided between electrodes 154 that are not diametrically opposed. For example, an electrical signal could be provided between electrode 154d and electrode 154a in FIG. 2. As will be recognized, an electrical signal could be provided between electrodes 154 in other arrangements in which the electrodes receiving an electrical signal are not diametrically opposed.

Alternatively, an electrical signal may be provided to the electrodes 154 of an implantable stimulator such that the electrical signal is provided between a centrally located electrode 154' and a concentrically arranged electrode 154. For example, an electrical signal could be provided between the concentrically arranged electrode 154i and the centrally located electrode 154'j in FIG. 3. As will be recognized, an electrical signal could be provided between electrodes 154 in other arrangements in which the electrodes receiving an electrical signal include a centrally located electrode 154' and a concentrically arranged electrode 154.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead comprising:
an array body disposed at a distal end of the lead, wherein the array body has a substantially flat, front surface; and
a plurality of electrodes concentrically arranged on the substantially flat, front surface of the array body,
wherein the lead comprises sixteen or fewer electrodes disposed on the substantially flat, front surface of the array body,
wherein at least one electrode is a non-circular electrode having a major axis and a minor axis,
wherein each of the at least one electrode defines two linear, parallel side boundaries of that electrode and two opposing half-circle curved end boundaries of that electrode, each curved end boundary connected to the two side boundaries,
and wherein the array body is molded around the plurality of electrodes.

2. The lead of claim 1, wherein the plurality of electrodes are arranged symmetrically with respect to one or more central axes.

3. The lead of claim 1, wherein at least two electrodes are diametrically opposed.

4. The lead of claim 1, wherein no two electrodes are diametrically opposed.

5. The lead of claim 1, further comprising a center electrode disposed on the array body and centrally located with respect to the plurality of electrodes.

6. The lead of claim 1, wherein the plurality of electrodes are concentrically arranged in more than one concentric ring.

7. The lead of claim 6, wherein at least one electrode in a first concentric ring is aligned coaxially with at least one electrode in a second concentric ring.

8. The lead of claim 1, wherein the front surface of the array body is circular.

9. The lead of claim 1, wherein the front surface of the array body is elliptical.

10. The lead of claim 1, wherein the lead is configured and arranged for implantation in proximity to a spinal cord to provide electrical stimulation of the spinal cord.

11. The lead of claim 1, wherein the lead is configured and arranged for implantation in proximity to a nerve to provide electrical stimulation of the nerve.

12. A lead comprising:
an array body disposed at a distal end of the lead, wherein the array body has a substantially flat, front surface; and
a plurality of electrodes concentrically arranged on the substantially flat, front surface of the array body,
wherein the lead comprises sixteen or fewer electrodes disposed on the substantially flat, front surface of the array body,
wherein at least one electrode is a non-circular electrode having a major axis and a minor axis,
wherein the plurality of electrodes are arranged in more than one concentric ring, and wherein the major axis of at least one non-circular electrode in a first one of the concentric rings is arranged radially and the major axis of at least one non-circular electrode in a second one of the concentric rings is arranged tangentially,
and wherein the array body is molded around the plurality of electrodes.

13. A lead comprising:
an array body disposed at a distal end of the lead, wherein the array body has a substantially flat, front surface; and
a plurality of electrodes concentrically arranged on the substantially flat, front surface of the array body,
wherein the lead comprises sixteen or fewer electrodes disposed on the substantially flat, front surface of the array body,
wherein the plurality of electrodes are concentrically arranged in more than one concentric ring, wherein each electrode in the more than one concentric ring is a non-circular electrode having a major axis and a minor axis and wherein the major axis of each electrode in a first concentric ring is not aligned coaxially with a major axis of a nearest electrode in a second concentric ring, and wherein the array body is molded around the plurality of electrodes.

14. A system for stimulation comprising:

an implantable pulse generator; and the lead of claim 1.

15. A lead for spinal cord stimulation, the lead comprising:

an array body disposed at a distal end of the lead; and a plurality of electrodes concentrically arranged on the array body, wherein the lead is configured and arranged for implantation in proximity to the spinal cord to provide electrical stimulation of the spinal cord, wherein the plurality of electrodes are arranged in more than one concentric ring, and wherein the major axis of at least one electrode in a first one of the concentric rings is arranged radially and the major axis of at least one electrode in a second one of the concentric rings is arranged tangentially.

16. The lead of claim 15, wherein the array body has a substantially flat front surface and the plurality of electrodes are disposed on the substantially flat front surface of the array body.

17. A lead comprising an array body disposed at a distal end of the lead, the array body comprising a plurality of electrodes, a carrier molded around the plurality of electrodes but not completely covering a front surface or a back surface of the electrodes, and a biocompatible material disposed over, and in contact with, the carrier, wherein the array body has a substantially flat, front surface;

wherein the lead comprises sixteen or fewer electrodes concentrically arranged on the substantially flat, front surface of the array body, and wherein the carrier and the biocompatible material are different.

* * * * *